United States Patent
Kang et al.

(10) Patent No.: US 9,194,827 B2
(45) Date of Patent: Nov. 24, 2015

(54) SCANNING DEVICE USING RADIATION BEAM FOR BACKSCATTER IMAGING AND METHOD THEREOF

(75) Inventors: Kejun Kang, Bejing (CN); Zhiqiang Chen, Bejing (CN); Yuanjing Li, Bejing (CN); Ziran Zhao, Bejing (CN); Yinong Liu, Bejing (CN); Wanlong Wu, Bejing (CN); Dong Lin, Bejing (CN); Le Tang, Bejing (CN); Chao Tu, Bejing (CN); Zongjun Shen, Bejing (CN); Guangwei Ding, Bejing (CN); Yingkang Jin, Bejing (CN); Xilei Luo, Bejing (CN); Shuo Cao, Bejing (CN)

(73) Assignees: NUCTECH COMPANY LIMITED, Haidian District, Beijing (CN); TSINGHUA UNIVERSITY, Haidian District, Beijing (CN)

( * ) Notice: Subject to any disclaimer, the term of this patent is extended or adjusted under 35 U.S.C. 154(b) by 480 days.

(21) Appl. No.: 13/519,305

(22) PCT Filed: Jun. 28, 2010

(86) PCT No.: PCT/CN2010/074570
§ 371 (c)(1),
(2), (4) Date: Jun. 26, 2012

(87) PCT Pub. No.: WO2011/079603
PCT Pub. Date: Jul. 7, 2011

(65) Prior Publication Data
US 2012/0288066 A1  Nov. 15, 2012

(30) Foreign Application Priority Data
Dec. 30, 2009  (CN) .......................... 2009 1 0244502

(51) Int. Cl.
*G01N 23/203* (2006.01)
*G21K 1/04* (2006.01)

(52) U.S. Cl.
CPC .............. *G01N 23/203* (2013.01); *G21K 1/043* (2013.01)

(58) Field of Classification Search
CPC .... G21K 1/043; G01N 23/203; G01V 5/0025
See application file for complete search history.

(56) References Cited

U.S. PATENT DOCUMENTS

| 3,808,444 A | 4/1974 | Schneeberer et al. |
| 4,745,631 A | 5/1988 | Paolini |

(Continued)

FOREIGN PATENT DOCUMENTS

| CN | 101113961 A | 1/2008 |
| CN | 201173903 Y | 12/2008 |

(Continued)

OTHER PUBLICATIONS

European Search Report for corresponding European Application No. EP 10 84 0392, dated Apr. 2, 2013.

(Continued)

*Primary Examiner* — Glen Kao
*Assistant Examiner* — Chih-Cheng Kao
(74) *Attorney, Agent, or Firm* — Knobbe, Martens, Olson & Bear, LLP (57) ABSTRACT

Disclosed is a scanning device using radiation beam for backscatter imaging. The scanning device includes a radiation source; a stationary shield plate and a rotary shield body positioned respectively between the radiation source and the subject to be scanned, wherein the stationary shield plate is fixed relative to the radiation source, and the rotary shield body is rotatable relative to the stationary shield plate. The ray passing area permitting the rays from the radiation source to pass through the stationary shield plate is provided on the stationary shield plate, and ray incidence area and ray exit area are respectively provided on the rotary shield body. During the process of the rotating and scanning of the rotary shield body, the ray passing area of the stationary shield plate intersects with the ray incidence area and the ray exit area of the rotary shield body to form scanning collimation holes. Further, a scanning method using radiation beam for backscatter imaging is also provided.

12 Claims, 3 Drawing Sheets

(56) References Cited

U.S. PATENT DOCUMENTS

| | | | |
|---|---|---|---|
| 4,750,196 A | 6/1988 | Harding | |
| 4,995,066 A | 2/1991 | Harding et al. | |
| 5,038,370 A | 8/1991 | Harding et al. | |
| 5,493,596 A | 2/1996 | Annis | |
| 2008/0043913 A1 | 2/2008 | Annis | |

FOREIGN PATENT DOCUMENTS

| | | |
|---|---|---|
| CN | 201285377 Y | 8/2009 |
| CN | 101644687 A | 2/2010 |
| DE | 3443095 A1 | 5/1986 |
| JP | 5296946 A2 | 11/1993 |
| WO | WO 01/37287 A1 | 5/2001 |
| WO | WO 2011/115923 A1 | 9/2011 |

OTHER PUBLICATIONS

European Patent Office Communication in related European Application No. 10 840 392.4-1554, dated Jan. 14, 2014.

Office Action in corresponding European Patent Application No. 10 840 392.4-1554, dated Sep. 9, 2014.

Summons to Attend Oral Proceedings Pursuant to Rule 115(1) EPC in European Application 10840392.4 dated Apr. 8, 2015 in 11 pages.

SCANNING DEVICE USING RADIATION BEAM FOR BACKSCATTER IMAGING AND METHOD THEREOF

FIELD OF THE INVENTION

The present invention generally relates to the field of application of radiation engineering, and particularly, to a non-destructive inspection device and a method thereof, and more particularly, to a scanning device using radiation beam for backscatter imaging and a method thereof.

BACKGROUND

In the application of non-destructive inspection and human body inspection, two types of technologies are generally utilized: an imaging technology using radiation beam for transmission and an imaging technology using radiation beam for backscattering. Where backscatter imaging is employed, a subject to be inspected is scanned by radiation beam, i.e. a pencil beam, simultaneously the detector receives signal representative of radiation scattered back from the subject. A scatter image can be reconstructed or obtained based on the detected signals which are correlated with scanned positions or portions of the subject to be inspected.

Conventional flying-spot scanning mechanism implements a first dimension scanning by rotation motion of the rotary shield body with multiple collimation holes within a ray scanning sector while carrying out a second dimension scanning by swing or translating the ray scanning sector.

However, in the arrangement of the above-mentioned rotary shield body with multiple collimation holes, a relatively complex flying-spot formation mechanism is used and it has disadvantage on shielding of the X-ray and the leakage of the X-ray is hazardous to human body.

Further, when implementing the first dimension scanning, the scanning device carries out a non-uniform scanning on the subject in a vertical plane. More specifically, the scanning ray accelerates at the starting and ending of one single pencil beam scanning operation. As a result, the scanning spot will be further enlarged longitudinally at the starting and ending points of one single pencil beam scanning operation where geometric deformation of the scanning spot occurs. Accordingly, a longitudinal compression deformation due to variation of the scanning velocity of the scanning takes place in addition to the geometric deformation of the resultant image.

Furthermore, for the operation of the second dimension scanning, if a translational movement of the ray scanning sector is performed, the ray generator, the rotary shield body, and so on is required to translate in the second dimension, this renders the mechanical configuration of this device rather complicate; and if a rotation motion of the ray scanning sector is performed, rotational inertia of the ray generator and the rotary shield body should be overcome. This gives rise to a problem concerning wear and tear or breakdown of bearings of the rotating driver and the rotating ray generator and the rotary shield body.

In addition, in the prior art, the radiation source, for example the X-ray tube, is generally disposed inside the rotary radiation body, so it is difficult to match interface of the scanning mechanism with that of the conventional X-ray tube. Consequently, it necessitates redesigning the shield body of the X-ray tube so as to achieve matching the same with the interface of a conventional X-ray tube, which in turn increases the cost of the scanning device for backscatter imaging.

SUMMARY OF THE INVENTION

The present invention has been made to overcome or alleviate at least one aspect of the above mentioned disadvantages or problems existing in the prior art.

Accordingly, it is an object of the present invention to provide a scanning device using radiation beam for backscatter imaging and a method thereof, which adopts a novel "flying-spot" formation mechanism so as to achieve the radiation beam scanning for backscattering.

Accordingly, it is another object of the present invention to provide radiation beam scanning device and method in which a linear moving flying-spot is achieved.

Accordingly, it is still another object of the present invention to provide a scanning device and scanning method for controlling sectional shape of the radiation beam passing through the scanning collimation holes and irradiating on the subject to be scanned by constraining shapes of the scanning collimation holes at different positions.

According to one aspect of the present invention, there is provided a scanning device using radiation beam for backscatter imaging, the scanning device comprising:

a radiation source; and a stationary shield plate and a rotary shield body positioned respectively between the radiation source and a subject to be scanned, wherein the stationary shield plate is fixed relative to the radiation source, and the rotary shield body is rotatable relative to the stationary shield plate; wherein:

a ray passing area permitting the radiation beams from the radiation source to pass through the stationary shield plate is provided on the stationary shield plate; and a ray incidence area and a ray exit area are respectively provided on the rotary shield body; during the process of the rotating and scanning of the rotary shield body, the ray passing area of the stationary shield plate intersects consecutively the ray incidence area and the ray exit area of the rotary shield body to form scanning collimation holes.

According to one preferred embodiment of the present invention, the ray passing area of the stationary shield plate is a linear slit; the rotary shield body is a cylinder, and the ray incidence area and the ray exit area are spiral slits. When the rotary shield body rotates in a uniform velocity, the scanning collimation holes consecutively move along the linear slit.

According to one preferred embodiment of the present invention, the stationary shield plate is provided between the radiation source and the rotary shield body.

Preferably, the scanning device using radiation beam for backscatter imaging further comprises: a control unit which controls scanning velocity of the radiation beam by controlling rotary velocity of the rotary shield body and acquires exit direction of the radiation beam by detecting rotary angle of the rotary shield body.

According to one preferred embodiment of the present invention, by controlling widths of the spiral slits of the rotary shield body at different positions, shapes of the scanning collimation holes at different positions are controlled such that sectional shape of the radiation beam passing through the scanning collimation holes and irradiating on the subject to be scanned is controlled.

Moreover, the scanning device further comprises: a drive unit adapted for driving the rotary shield body to rotate; wherein the rotary shield body is a hollow cylinder or a solid cylinder.

Specifically, rotary axis of the rotary shield body is located on a coplanar plane which is defined by the radiation source and the linear slit of the stationary shield plate.

According to another aspect of the present invention, there is provided a scanning method using radiation beam for backscatter imaging, the scanning method comprising the steps of:

providing a radiation source which emits radiation beam;

providing a stationary shield plate and a rotary shield body positioned respectively between the radiation source and a subject to be scanned, wherein the stationary shield plate is fixed relative to the radiation source, and the rotary shield body is rotatable relative to the stationary shield plate; wherein a ray passing area permitting the radiation beams from the radiation source to pass through the stationary shield plate is provided on the stationary shield plate, and, a ray incidence area and a ray exit area are respectively provided on the rotary shield body; and rotating the rotary shield body such that the ray passing area of the stationary shield plate intersects consecutively the ray incidence area and the ray exit area of the rotary shield body to form scanning collimation holes.

Preferably, the ray passing area of the stationary shield plate is a linear slit; the rotary shield body is a cylinder, and the ray incidence area and the ray exit area are spiral slits. When the rotary shield body rotates in a uniform velocity, the scanning collimation holes consecutively move along the linear slit.

According to one preferred embodiment of the present invention, the scanning method further comprises the steps of: detecting positions of the scanning collimation holes; and, controlling exit direction of the radiation beam based on detection of positions of the scanning collimation holes.

Preferably, the scanning method further comprises the steps of: arranging the scanning collimation holes in a manner such that these holes have predetermined shapes relative to the radiation source, as a result, sectional shape of the radiation beam passing through the scanning collimation holes and irradiating on the subject to be scanned has a predetermined shape.

As apparent from the above-mentioned unspecified embodiments, the present invention at least has the one or more following advantages and effects:

1. The present invention provides scanning device and method with novel "flying-spot" formation mechanism, which adopts a simplified scanning mechanism for backscatter imaging and achieves good effect for shielding radiation.

2. According to one preferred embodiment of the present invention, the scanning device and method may enable a controllable scanning for the subject to be scanned and a convenient sampling for the subject to be scanned in accordance with the predetermined mode, thereby backscatter image data as desired can be obtained. For example, the scanning device and method of the present invention may perform scanning on the subject to be scanned in a uniform velocity, which brings conveniently the uniform sampling for the subject to be scanned and avoids longitudinal compression deformation in the obtained backscatter image.

3. In accordance with different application needs, different rotary shield bodies with different spiral lines or with different slits may be manufactured, the rotary shield body of the scanning mechanism according to the present invention is replaceable to meet different application needs.

4. According to the present invention, during the operation of the second dimension scanning in which swing movement of the ray scanning sector is to be carried out, since the ray scanning sector and the rotary shield body perform rotation movement in the same plane, direction of angular momentum of the rotary shield body will not change by the rotary ray scanning on the ray scanning sector. As such, it is not required to overcome rotational inertia of the rotary shield body when the ray scanning sector is to be swung, and, the operation of the second dimension scanning may be easily done by swinging the ray scanning sector.

5. In accordance with the present invention, as radiation source is not disposed inside the rotary shield body, scanning mechanism may be equipped with mechanical interface that matches that of conventional X-ray tube, without redesigning the shield body for the X-ray tube. Accordingly, a compact structure is achieved while the cost may be greatly reduced.

DETAILED DESCRIPTION OF PREFERRED EMBODIMENTS OF THE INVENTION

Exemplary embodiments of the present disclosure will be described hereinafter in detail with reference to the attached FIGS. 1-3, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

Figure 1:
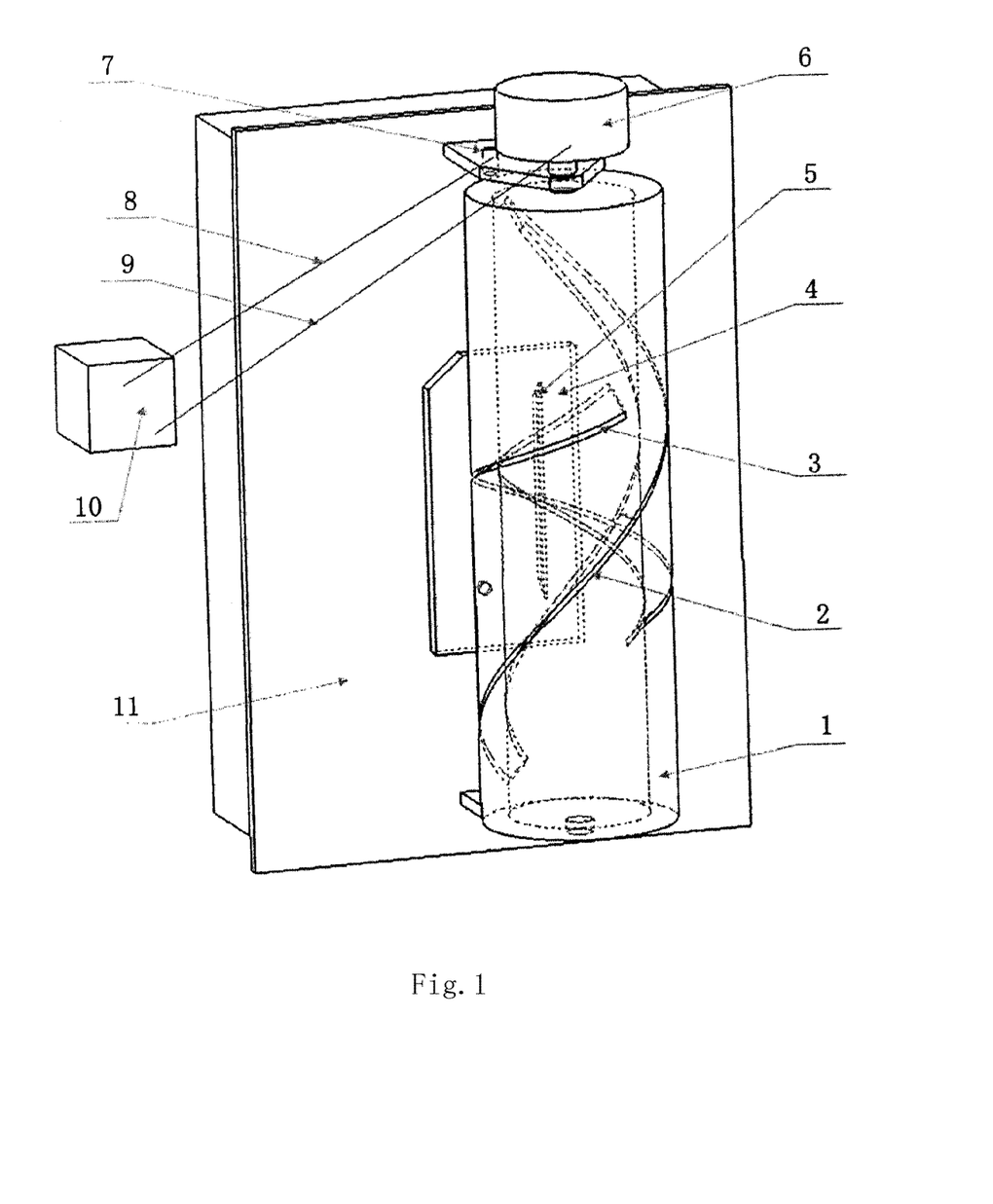
FIG. 1 is structural perspective view of a scanning device using radiation beam for backscatter imaging according to a preferred embodiment of the present invention.
Figure 2:
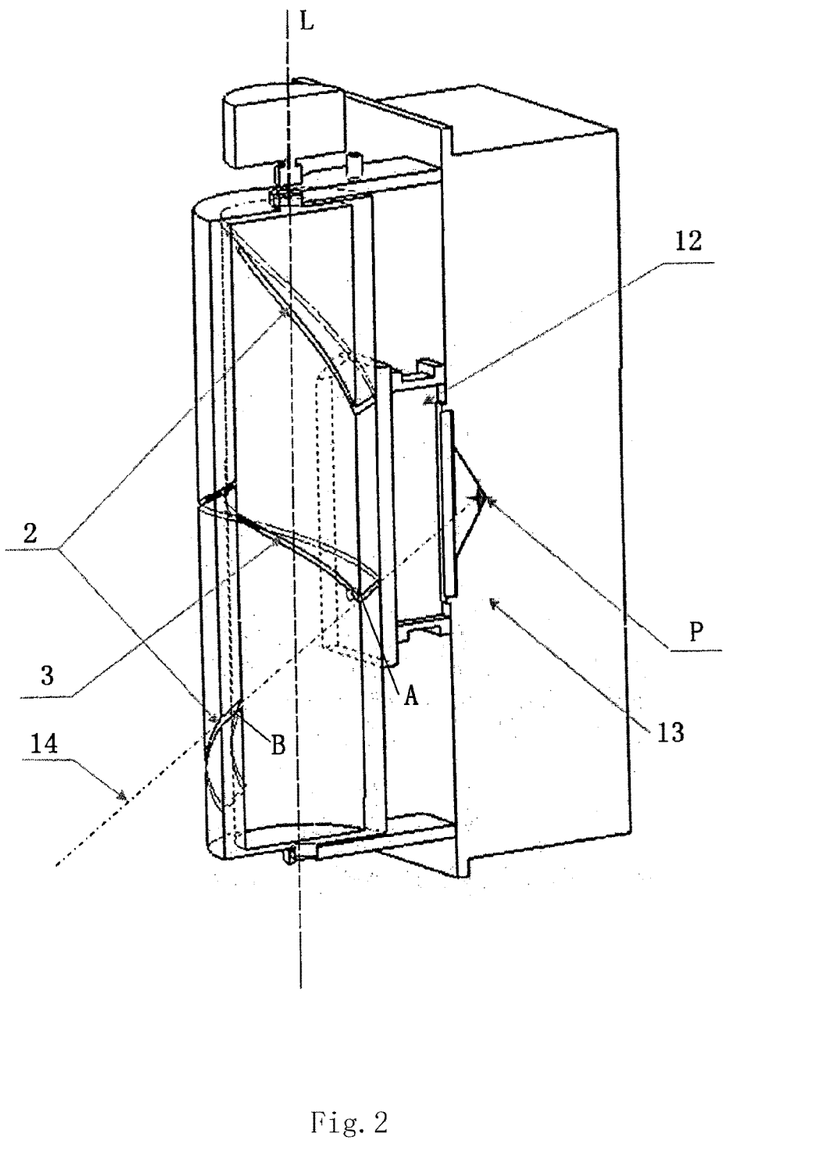
FIG. 2 is a cross-sectional view of the scanning device of FIG. 1.
Figure 3:
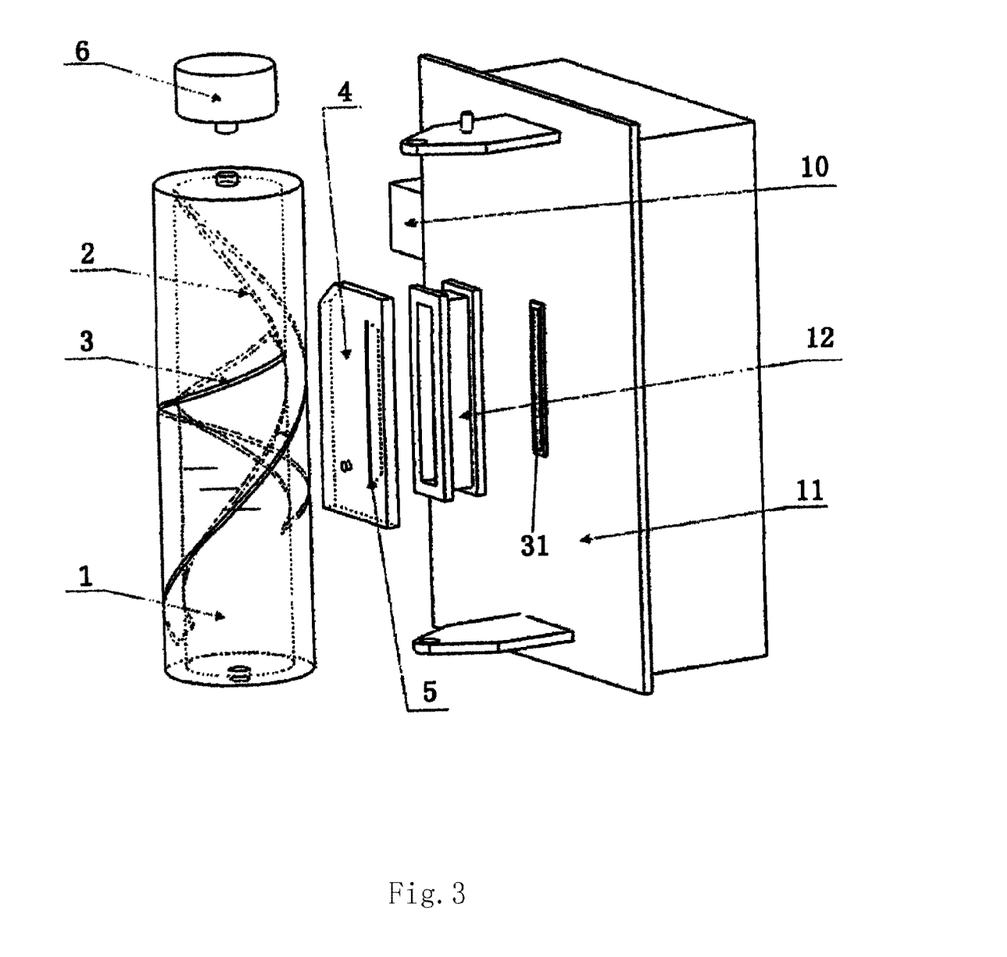
FIG. 3 is an exploded perspective view of arrangements and configurations of the backscatter scanning device of FIG. 1.

Referring to FIGS. 1-3 of the drawings, a scanning device using radiation beam for backscatter imaging according to a preferred embodiment of the present invention is illustrated. The scanning device comprises: a radiation source 13 (for example, an X-ray tube), a stationary shield plate 5 and a rotary shield body 1 positioned respectively between the radiation source 13 and a subject to be scanned (no shown, for example at the left side of FIG. 2). The stationary shield plate 4 is fixed relative to the radiation source 13, and the rotary shield body 1 is rotatable relative to the stationary shield plate 4. Further, a ray passing area permitting the radiation beams from the radiation source 13 to pass through the stationary shield plate 4 (for example the longitudinal slit 5 of FIGS. 1-3) is provided on the stationary shield plate 4. A ray incidence area (for example the slit 3 of FIGS. 1-3) and a ray exit area (for example the slit 2 of FIGS. 1-3) are respectively provided on the rotary shield body 1; during the process of the rotating and scanning of the rotary shield body 1, the ray passing area 5 of the stationary shield plate 4 intersects consecutively with the ray incidence area 3 and the ray exit area 2 of the rotary shield body 1 to form scanning collimation holes. In the above-mentioned embodiment, the stationary shield plate 4 is provided between the radiation source 13 and the rotary shield body 1.

In the above embodiment of the present invention, a ray generator, such as an X-ray tube, includes a ray generator housing 11 and the radiation source 13 accommodated in the ray generator housing 11. In the above-mentioned arrangement, the radiation source 13 may be a X-ray tube, y-ray source or, isotopic source, etc. As shown in FIGS. 1 and 3, in one preferred embodiment, the ray generator housing 11 has a substantially rectangular case shape, and a collimation slit 31 is provided on the ray generator housing 11 such that the radiation ray emitted from the radiation source 13 exits through the collimation slit 31 of the ray generator housing 11. Radiation beam 14 emitted from a target point P of the radiation source 13 passes through the collimation slit 31 to form a ray sector, and then goes through the ray passing area (for example the longitudinal slit 5 of FIGS. 1-3) through the stationary shield plate 4, the ray incidence area (for example the slit 3 of FIGS. 1-3), and the ray exit area (for example the slit 2 of FIGS. 1-3). By provision of the longitudinal slit 5 of the stationary shield plate 4, the relative position relationship between the slits 3 and 2 is made such that during the process of the rotating and scanning of the rotary shield body 1, the ray passing area 5 of the stationary shield plate 4 intersects consecutively with the ray incidence area 3 and the ray exit area 2 of the rotary shield body 1 to form scanning collimation holes. In other words, the ray incidence spiral slit 3 and the ray exit spiral slit 2 of the rotary shield body 1 and the longitudinal slit 5 of the stationary shield plate 4 together constitute a radiation beam collimation hole.

As shown in FIGS. 1-3, the ray passing area 5 of the stationary shield plate 4 is a linear slit, the rotary shield body 1 is a cylinder, and the ray incidence area 3 and the ray exit area 2 are spiral slits. Referring to FIG. 2, specifically, any point at the ray incidence area 3, and the ray exit area 2, for example, point A and point B, run in a uniform circular motion along the cylindrical face of the rotary shield body 1, and simultaneously, run in a linear motion in accordance with certain velocity distribution as required along the radial direction of the rotary shield body 1, so as to form a certain cylindrically spiral line. In one preferred embodiment, any point at the ray incidence area 3 and the ray exit area 2, for example, point A and point B, may run in a uniform circular motion along the cylindrical face of the rotary shield body 1, and simultaneously, run in a linear motion at a uniform velocity along the radial direction of the rotary shield body 1, so as to form a uniform speed cylindrically spiral line.

Referring to FIG. 2, after determination of the target point P of the radiation source 13 and the point A of the ray incidence area 3, by linking the target point P of the radiation source 13 with the point A of the ray incidence area 3 to form a radiation beam 14 in a linear direction, the point B of the ray exit area 2 can be determined.

Since the ray incidence area 3 and the ray exit area 2 are configured to be the uniform speed cylindrically spiral line slits, when the rotary shield body 1 rotates in a uniform velocity, positions of the scanning collimation holes move with rotation of the rotary shield body 1, Accordingly the exit radiation beam 14 move, such that the scanning collimation holes consecutively and uniformly move along the linear slit 5.

Although the ray incidence area 3 and the ray exit area 2 are configured to be the uniform speed cylindrically spiral line slits in the above-mentioned embodiments, they are not limited to this according to the present invention. For example, the ray incidence area 3 and the ray exit area 2 may be configured to be the spiral lines with the above certain form, that is, any point at the ray incidence area 3 and the ray exit area 2 may run in a uniform circular motion along the cylindrical face of the rotary shield body 1, and simultaneously, run in a linear motion in accordance with certain velocity distribution along the radial direction of the rotary shield body 1, so as to form a certain cylindrically spiral line. As a result, when the rotary shield body 1 rotates in a uniform velocity, positions of the scanning collimation holes move with rotation of the rotary shield body 1. Accordingly the exit radiation beam 14 move, such that the scanning collimation holes move along the linear slit 5 in accordance with the predetermined velocity distribution. Accordingly, the scanning device according to the present invention may enable a controllable scanning for the subject to be scanned and a convenient sampling for the subject to be scanned in accordance with the predetermined mode, thereby backscatter image data as desired can be obtained. As a result, qualities and resolutions of the backscatter images are improved, and precision and efficiency of the backscatter detection are advanced, thus satisfying different application demands.

Moreover, the scanning device may further includes a drive unit 6 adapted for driving rotation of the rotary shield body 1, for example, speed-regulating motor and so on. In order to reduce rotary inertia of the rotary shield body 1, according to one preferred embodiment, the rotary shield body 1 is embodied in a hollow cylindrical form. However, according to the present invention, it is not limited to this. For example, the rotary shield body 1 may also be embodied as a solid cylinder.

Particularly, in the above-mentioned embodiment, referring to FIG. 1, the scanning device may further includes rotary coded disk readout unit 7 adapted for detecting rotation position of the rotary shield body 1, and a coded disk readout signal line 8 adapted for inputting information relating to rotation position of the rotary shield body 1 into a control unit 10. Since positions of the scanning collimation holes are determined by the rotational position of the rotary shield body 1. With the above arrangement, positions where the scanning collimation holes are formed can be detected. As shown in FIG. 1, the control unit 10 is also connected with the drive motor 6 via motor drive line 9, so as to further control rotation of the rotary shield body 1. By controlling rotary speed of the rotary shield body 1, scanning speed of the radiation beam may be controlled, and, by detecting rotation angle of the rotary shield body 1, exit direction of the radiation beam can be acquired. Referring to FIG. 2, in one preferred embodiment, rotary axis L of the rotary shield body 1 may be located on a coplanar plane which is defined in common by the radiation source 13 and the linear slit 5 of the stationary shield plate 4. As described above, the rotary shield body 1 may be embodied as a solid cylinder, or else, a hollow cylinder with certain thickness. By constraining widths of the spiral slits of the rotary shield body at different positions, shapes of the scanning collimation holes at different positions are controlled such that sectional shape of the radiation beam passing through the scanning collimation holes and irradiating on the subject to be scanned is controlled.

For example, the widths of the spiral slits 2 and 3 at both longitudinal ends of the rotary shield body 1 may be narrower than that of the slit at the longitudinally center position, and, the scanning collimation holes at the spiral slits 2 and 3 at both longitudinal ends of the rotary shield body 1 can be formed with a certain angle relative to these at the longitudinal middle part.

By adopting the above-mentioned arrangement, it ensures that the scanning collimation holes always aim at the target point from the radiation source and an unblocked passage for the radiation beam is formed therein. Further, sectional shapes of the radiation beams passing through the scanning collimation holes and irradiating on the subject to be scanned, at different positions, for example radiation beams emitting from both ends and the middle portions of the rotary shield body 1, are maintained constant and uniform. However, according to the present invention, it is not limited to this. For example, by limiting widths of the spiral slits of the rotary shield body at different positions, shapes of the scanning collimation holes at different positions are controlled, as a result, sectional shapes of the radiation beam passing through the scanning collimation holes and irradiating on the subject to be scanned are controlled to meet different scanning demands.

Referring to FIG. 3, the ray generator housing 11 may further be connected with the stationary shield plate 4 through a shield sleeve 12, so as to ensure the ray shielding effect. It can be seen from the above-mentioned arrangement, the radiation source 13 is disposed inside the ray generator housing 11, instead of inside the rotary shield body 1. The scanning mechanism may be equipped with a shield sleeve 12 with a mechanical interface that matches with that of conventional X-ray tube, without redesigning the shield body for the X-ray tube. As such, the scanning mechanism of the present invention has a compact structure, and the cost is greatly reduced.

With reference to the accompanying drawings, a scanning method using radiation beam for backscatter imaging according to the present invention will be described hereinafter Referring to FIGS. 1-3, the scanning method using radiation beam for backscatter imaging according to one preferred embodiment of the present invention, comprises the steps of: providing a radiation source 13 which emits radiation beam 14; providing a stationary shield plate 4 and a rotary shield body 1 positioned respectively between the radiation source 13 and a subject to be scanned, wherein the stationary shield plate 4 is fixed relative to the radiation source, and the rotary shield body 1 is rotatable relative to the stationary shield plate 4; wherein a ray passing area permitting the radiation beams 14 from the radiation source 13 to pass through the stationary shield plate 4 is provided on the stationary shield plate 4, and, a ray incidence area 3 and a ray exit area 2 are respectively provided on the rotary shield body 4; and, rotating the rotary shield body 4 such that the ray passing area 5 of the stationary shield plate 4 intersects consecutively with the ray incidence area 3 and the ray exit area 2 of the rotary shield body 4 to form scanning collimation holes.

In the above-mentioned scanning device, the ray passing area 5 of the stationary shield plate 4 is a linear slit; the rotary shield body 1 is a cylinder, and the ray incidence area 3 and the ray exit area 2 are spiral slits; and when the rotary shield body 1 rotates in a uniform velocity, the scanning collimation holes consecutively move along the linear slit 5 at a controllable speed.

Referring to FIG. 1, during the process of the scanning, by rotary coded disk readout unit 7 and coded disk readout signal line 8, control unit 10 may read out current state of the rotary shield body 1, accordingly the current positions of the scanning collimation holes are determined. Based on detection of positions of the scanning collimation holes, exit direction of the radiation beam can be further acquired. Furthermore, by arranging the scanning collimation holes in a manner such that these holes have predetermined shapes relative to the radiation source 13, as a result, sectional shape of the radiation beam 14 passing through the scanning collimation holes and irradiating on the subject to be scanned may be kept in a predetermined shape, so as to satisfy various demands for different scanning operation.

Although several exemplary embodiments have been shown and described, it would be appreciated by those skilled in the art that various changes or modifications may be made in these embodiments without departing from the principles and spirit of the disclosure, the scope of which is defined in the claims and their equivalents.

What is claimed is:

1. A scanning device configured for backscatter imaging, the scanning device consisting essentially of:
   a radiation source, wherein the radiation source emits x-ray radiation; and
   a stationary shield plate and a single rotary shield body positioned respectively between the radiation source and a subject to be scanned, wherein the stationary shield plate is fixed relative to the radiation source, and the single rotary shield body is rotatable relative to the stationary shield plate; wherein:
   a ray passing area, permitting radiation beams from the radiation source to pass through the stationary shield plate, is provided on the stationary shield plate; and
   a ray incidence area and a ray exit area are respectively provided on the rotary shield body, wherein the ray incidence area is formed by a first spiral slit and the ray exit area is formed by a second spiral slit,
   wherein, during a process of rotating and scanning of the rotary shield body, the ray passing area of the stationary shield plate intersects consecutively with the ray incidence area and the ray exit area of the single rotary shield body to form scanning collimation holes; and
   wherein the width of each of the first and second spiral slits at their longitudinal ends is narrower than the width of each of the slits at a longitudinally center position, and the scanning collimation holes at both longitudinal ends of each of the first and second spiral slits are formed at an angle relative to the collimation holes at the longitudinal center position of each of the first and second spiral slits.

2. The scanning device configured backscatter imaging according to claim 1, wherein:
   the ray passing area of the stationary shield plate is a linear slit;
   the single rotary shield body is a cylinder; and
   when the single rotary shield body rotates at a uniform velocity, the scanning collimation holes consecutively move along the linear slit.

3. The scanning device configured for backscatter imaging according to claim 2, further comprising:
   a drive unit adapted for driving rotation of the rotary shield body, wherein the single rotary shield body is hollow or a solid cylinder.

4. The scanning device configured for backscatter imaging according to claim 2, wherein:
   a rotary axis of the single rotary shield body is located on a coplanar plane which is defined in common by the radiation source and the linear slit of the stationary shield plate.

5. The scanning device configured for backscatter imaging according to claim 1, wherein:
   the stationary shield plate is provided between the radiation source and the rotary shield body.

6. The scanning device configured for backscatter imaging according to claim 5, further comprising:
   a control unit which controls scanning velocity of the radiation beam by controlling rotary velocity of the single rotary shield body and acquires exit direction of the radiation beam by detecting rotary angle of the rotary shield body.

7. The scanning device configured for backscatter imaging according to claim 6, wherein:
   by limiting widths of the spiral slits of the single rotary shield body at different positions, shapes of the scanning collimation holes at different positions are controlled such that sectional shape of the radiation beam passing through the scanning collimation holes and irradiating on the subject to be scanned is controlled.

8. A scanning method for backscatter imaging, consisting essentially of:
providing a radiation source which emits a radiation beam, wherein the radiation source emits x-ray radiation;
providing a stationary shield plate and a single rotary shield body positioned respectively between the radiation source and a subject to be scanned, wherein the stationary shield plate is fixed relative to the radiation source, and the single rotary shield body is rotatable relative to the stationary shield plate; wherein a ray passing area permitting radiation beams from the radiation source to pass through the stationary shield plate is provided on the stationary shield plate, and a ray incidence area and a ray exit area are respectively provided on the rotary shield body, wherein the ray incidence area is formed by a first spiral slit and the ray exit area is formed by a second spiral slit; and
rotating the single rotary shield body such that the ray passing area of the stationary shield plate intersects consecutively with the ray incidence area and the ray exit area of the single rotary shield body to form scanning collimation holes;
wherein the width of each of the first and second spiral slits at their longitudinal ends is narrower than the width of each of the slits at a longitudinally center position, and the scanning collimation holes at both longitudinal ends of each of the first and second spiral slits are formed at an angle relative to the collimation holes at the longitudinal center position of each of the first and second spiral slits.

9. The scanning method for backscatter imaging according to claim 8, wherein:
the ray passing area of the stationary shield plate is a linear slit;
the single rotary shield body is a cylinder; and
when the single rotary shield body rotates at a uniform velocity, the scanning collimation holes consecutively move along the linear slit.

10. The scanning method for backscatter imaging according to claim 8, wherein:
the stationary shield plate is provided between the radiation source and the rotary shield body.

11. The scanning method for backscatter imaging according to claim 10, further comprising the step of:
controlling scanning velocity of the radiation beam by controlling rotary velocity of the rotary shield body, and acquiring exit direction of the radiation beam by detecting rotary angle of the rotary shield body.

12. The scanning method for backscatter imaging according to claim 11, wherein:
by limiting widths of the spiral slits of the single rotary shield body at different positions, shapes of the scanning collimation holes at different positions are controlled such that sectional shape of the radiation beam passing through the scanning collimation holes and irradiating on the subject to be scanned is controlled.

* * * * *

UNITED STATES PATENT AND TRADEMARK OFFICE
CERTIFICATE OF CORRECTION

PATENT NO.         : 9,194,827 B2
APPLICATION NO.    : 13/519305
DATED              : November 24, 2015
INVENTOR(S)        : Kang et al.

Page 1 of 1

It is certified that error appears in the above-identified patent and that said Letters Patent is hereby corrected as shown below:

On the title page (Item 75), line 1, Change "Bejing" for Kejun Kang to --Beijing--.

(Item 75), line 2, Change "Bejing" for Zhiqiang Chen to --Beijing--.

(Item 75), line 2, Change "Bejing" for Yuanjing Li to --Beijing--.

(Item 75), line 3, Change "Bejing" for Ziran Zhao to --Beijing--.

(Item 75), line 4, Change "Bejing" for Yinong Liu to --Beijing--.

(Item 75), line 4, Change "Bejing" for Wanlong Wu to --Beijing--.

(Item 75), line 5, Change "Bejing" for Dong Lin to --Beijing--.

(Item 75), line 6, Change "Bejing" for Le Tang to --Beijing--.

(Item 75), line 6, Change "Bejing" for Chao Tu to --Beijing--.

(Item 75), line 7, Change "Bejing" for Zongjun Sherr to --Beijing--.

(Item 75), line 8, Change "Bejing" for Guangwei Ding to --Beijing--.

(Item 75), line 9, Change "Bejing" for Yingkang Jin to --Beijing--.

(Item 75), line 9, Change "Bejing" for Xilei Luo to --Beijing--.

(Item 75), line 10, Change "Bejing" for Shuo Cao to --Beijing--.

In the specification

Column 7 line 20, After "hereinafter" insert --.--.

In the claims

Column 8 line 32, Claim 2, change "backscatter" to --for backscatter--.

Signed and Sealed this
Fifth Day of July, 2016

Michelle K. Lee
*Director of the United States Patent and Trademark Office*